United States Patent [19]

Moguilewsky et al.

[11] Patent Number: 5,166,146
[45] Date of Patent: Nov. 24, 1992

[54] AMINO ACID CYCLOPENTANOPHENONTHRENE COMPOUNDS

[75] Inventors: Martine Moguilewsky, Paris; Lucien Nedelec, Le Raincy; François Nique, Pavillons sous Bois; Daniel Philibert, La Varenne Saint Hilaire, all of France

[73] Assignee: Roussel Uclaf, Paris, France

[21] Appl. No.: 568,597

[22] Filed: Aug. 16, 1990

[30] Foreign Application Priority Data

Aug. 23, 1989 [FR] France ................. 89 11173

[51] Int. Cl.$^5$ .................. A61K 31/56; C07J 1/00; C07J 9/00
[52] U.S. Cl. .................. 514/179; 552/642; 552/643; 552/648
[58] Field of Search .......... 552/642, 643, 648; 514/179

[56] References Cited

PUBLICATIONS

Loozen et al., Chemical Abstract vol. 109, 1988 #CA 109(19): 170799.

Primary Examiner—Nicholas S. Rizzo
Assistant Examiner—Y. N. Gupta
Attorney, Agent, or Firm—Bierman and Muserlian

[57] ABSTRACT

A compound of the formula

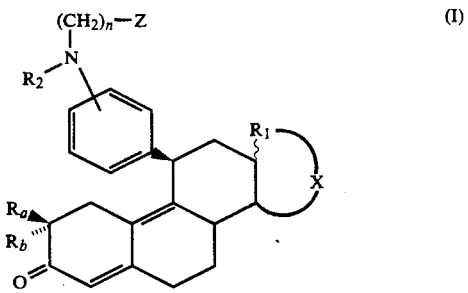

wherein $R_1$ is an aliphatic hydrocarbon of 1 to 8 carbon atoms, $R_a$ and $R_b$ are individually hydrogen or alkyl of 1 to 4 carbon atoms, $R_2$ is hydrogen or optionally substituted alkyl of 1 to 12 carbon atoms, n is an integer from 1 to 6, Z is free carboxy or salified with an alkali metal, alkaline earth metal or $NH_4$ and X is the remainder of an optionally substituted and optionally unsaturated 5 or 6-member ring and the wavy line indicates the α- or β-position for $R_1$ having anti-glucocorticoid activity.

19 Claims, No Drawings

AMINO ACID CYCLOPENTANOPHENONTHRENE COMPOUNDS

STATE OF THE ART

Related prior art include British Patent No. 2,160,873, German Patent Application DE-A 3,619,413 and U.S. Pat. No. 4,921,846.

OBJECTS OF THE INVENTION

It is an object of the invention to provide the novel omega-phenylamino-alkanoic acids of formula I and a novel process and intermediates for their preparation.

It is another object of the invention to provide novel anti-glucocorticoid compositions and to provide a novel method of inducing anti-glucocorticoid activity in warm-blooded animals.

These and other objects and advantages of the invention will become obvious from the following detailed description.

THE INVENTION

The novel compounds of the invention of the formula

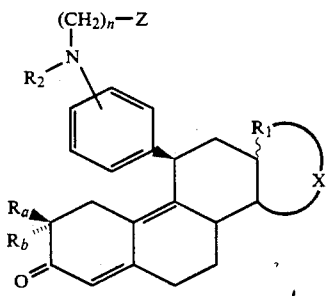

(I)

wherein $R_1$ is an aliphatic hydrocarbon of 1 to 8 carbon atoms, $R_a$ and $R_b$ are individually hydrogen or alkyl of 1 to 4 carbon atoms, $R_2$ is hydrogen or optionally substituted alkyl of 1 to 12 carbon atoms, n is an integer from 1 to 6, Z is free carboxy or salified with an alkali metal, alkaline earth metal or $NH_4$ and X is the remainder of an optionally substituted and optionally unsaturated 5 or 6-member ring and wavy line indicates the α- or β-position for $R_1$.

$R_1$ preferably is linear or branched alkyl of 1 to 4 carbon atoms such as methyl, ethyl, propyl, isopropyl or butyl and $R_1$ is in the β-position preferably. When $R_a$ and $R_b$ are alkyl, it is preferably methyl but $R_a$ and $R_b$ can also be ethyl, propyl, isopropyl or butyl.

When $R_2$ is optionally substituted alkyl, it is preferably methyl, ethyl or propyl. When the alkyl is an ethyl or propyl, it is optionally substituted by a dimethylamino or diethylamino or by pyrrolidinyl, piperidinyl, piperazinyl or morpholinyl.

When Z is a salified carboxy group, it is preferably the salt of sodium, potassium, calcium, magnesium, ammonium or an amine salt such as the salts of lysine, arginine, cysteine, betaine, carnitine, meglumine, quinine, sarcosine, procaine, histidine or N-methyl glucamine.

A preferred group of compounds of the invention have the formula

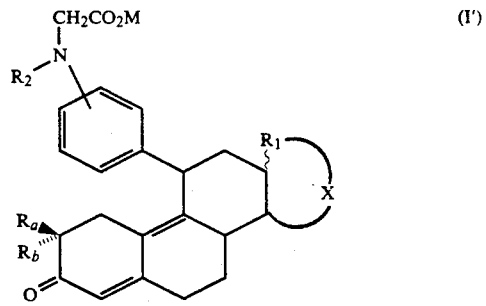

(I')

wherein M is hydrogen or sodium and preferably the products of formula I in which X is the remainder of the formula

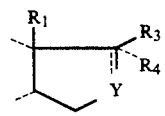

in which $R_1$ has the above definition, the dotted line in position 16-17 symbolizes the optional presence of a double bond, Y is

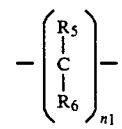

in which $n_1$ is 1 or 2, $R_5$ is hydrogen, alkyl of 1 to 8 carbon atoms, alkenyl or alkynyl of 2 to 8 carbon atoms, aryl of 6 to 14 carbon atoms or aralkyl of 7 to 15 carbon atoms, $R_6$ can individually have the definition of $R_5$ or —OH and $R_3$ and $R_4$ individually are hydrogen, or —OH, $OAlk_1$, $O—CO—Alk_2$ in which $Alk_1$ and $Alk_2$ are alkyl of 1 to 8 carbon atoms or aralkyl of 7 to 15 carbon atoms, or alkyl, alkenyl or alkynyl of 2 to 8 carbon atoms and optionally substituted or

or a —$COCH_2OCOAlk_3$ in which $Alk_3$ is optionally substituted alkyl of 1 to 8 carbon atoms or aralkyl of 7 to 15 carbon atoms, or $CO—CO_2H$, or a $CO—CO_2—Alk_4$ in which $Alk_4$ is alkyl of 1 to 8 carbon atoms or

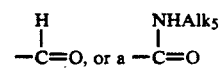

in which $Alk_5$ is alkyl of 1 to 8 carbon atoms or aralkyl of 7 to 15 carbon atoms, or —C≡N, or $R_3$ and $R_4$ together with the carbon atom to which they are attached form

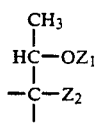

in which $Z_1$ is hydrogen, alkyl of 1 to 8 carbon atoms or acyl of an organic carboxylic acid of 1 to 8 carbon atoms and $Z_2$ is alkyl of 1 to 8 carbon atoms, or $R_3$ and $R_4$ form together with the carbon atom to which they are attached:

in which U is —(CH$_2$)$_{n_2}$— in which $n_2$ is an integer of 1, 2, 3 or 4 or —CH=CH—(CH$_2$)$_{n_3}$— in which $n_3$ is 1 or 2, or

When $R_5$ or $R_6$ is alkyl, it is preferably methyl or ethyl. When $R_5$ or $R_6$ is alkenyl, it is preferably vinyl, isopropenyl or allyl. When $R_5$ or $R_6$ is alkynyl, it is preferably ethynyl or propynyl. When $R_5$ or $R_6$ is aryl or aralkyl, it is preferably phenyl or benzyl.

When $R_3$ or $R_4$ is OAlk$_1$ or OCOAlk$_2$, Alk$_1$ and Alk$_2$ preferably are methyl, ethyl, n-propyl, butyl, pentyl, hexyl or benzyl. When $R_3$ or $R_4$ is optionally substituted alkyl, alkenyl or alkynyl, it is preferably —C≡C—W, —CH=CH—W or —CH$_2$—CH$_2$—W in which W is hydrogen, halogen, trialkylsilyl of 3 to 12 carbon atoms, linear or branched alkyl of 1 to 6 carbon atoms, or phenyl, the said alkyl and phenyl being optionally substituted. Alk$_3$, Alk$_4$ and Alk$_5$ preferably are one of the preferred values of Alk$_1$ and Alk$_2$. Y very preferably is methylene.

A more preferred group of compounds of formula I are those wherein the D ring of the steroid nucleus does not carry any unsaturation, $R_5$ and $R_6$ are hydrogen and $n_1$ is 1, and especially those of the formula

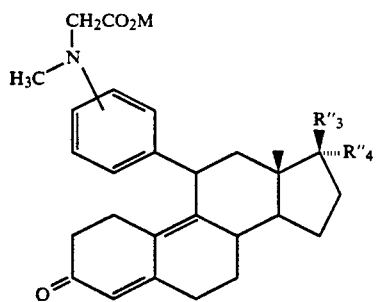

(I'')

in which M is as defined previously and either R''$_3$ is hydroxy and R''$_4$ is either a C≡C—R$_7$ group in which the dotted lines indicate the optional presence of a second or third bond and R$_7$ is hydrogen, halogen, trimethylsilyl or methyl optionally substituted by one or more halogens, hydroxy or by alkoxy, alkylthio or alkylamino of 1 to 4 carbon atoms, dialkylamino of 2 to 8 carbon atoms or trialkylsilyl of 3 to 12 carbon atoms or 2-propynyl or 2-propenyl, or R''$_3$ and R''$_4$ together with the atom to which they are attached are

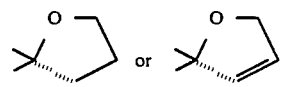

Among the specific preferred compounds of the invention is the sodium salt of [[4-[17α-(1-propynyl)-Δ$^{4,9}$-estradien-17β-ol-3-one 11β-yl]-phenyl]-methylamino]-acetic acid.

The novel process for the preparation of the compounds of formula I comprises reacting a compound of the formula

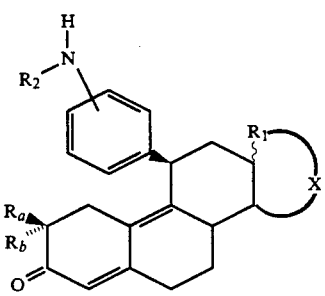

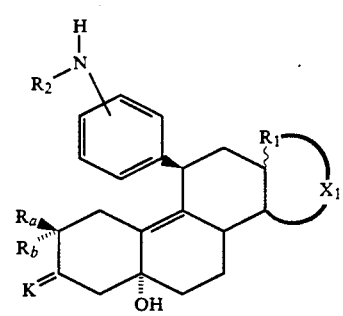

wherein $R_2$, $R_1$, $R_a$, $R_b$ and X are as defined above, $X_1$ has the meaning for X as well as those values in which the reactive functions are protected and K is a protected oxo in the presence of a base with a halo-ester of the formula

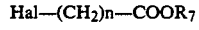

Hal—(CH$_2$)n—COOR$_7$   III wherein Hal is halogen, n has the above meaning and R$_7$ is alkyl of 1 to 4 carbon atoms and optionally substituted by one or more phenyls to obtain the products of formulae IV$_a$ and IV$_b$ respectively:

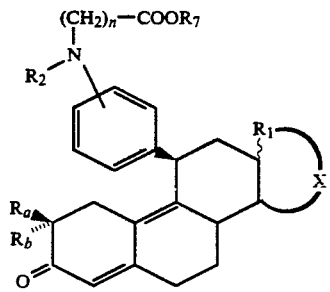

-continued

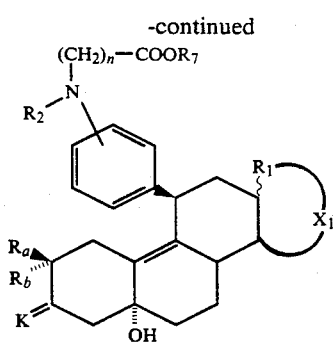

subjecting the latter to dehydration and an optional deprotection reaction for the protected reactive functions, to obtain the products of formulae IV$_a$, which are subjected to a basic treatment then, if desired, an acid treatment to obtain the products of formula I.

In a preferred method for carrying out the process, the products of formulae II''$_a$ and II''$_b$

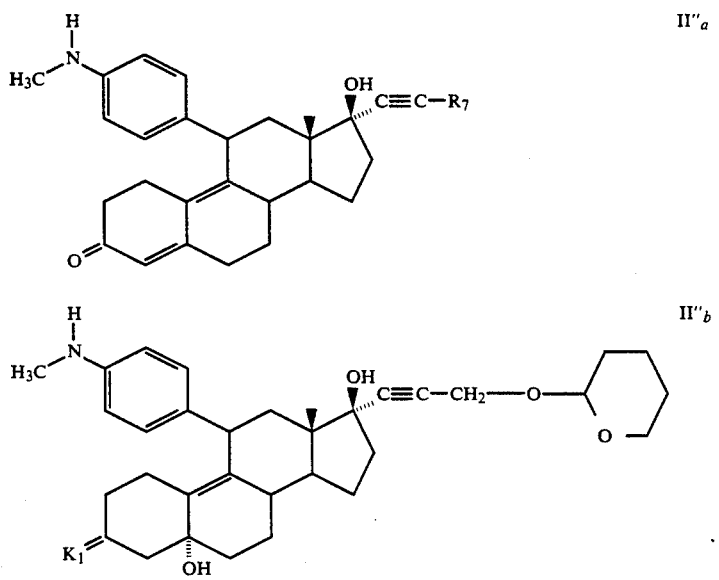

wherein K$_1$ is protected oxo in the form of an ethylenedioxy or dimethyl acetal are reacted with ethyl bromoacetate in the presence of a nitrogenated base to obtain the products of formula IV''$_a$ and IV''$_b$ respectively:

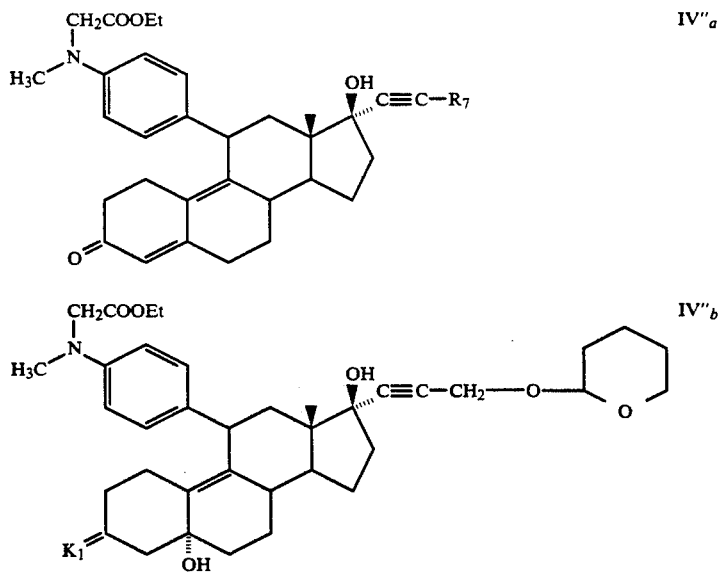

which products, if desired, are hydrogenated to obtain, according to the catalyst used, either the products of formulae V''$_a$ and V''$_b$ respectively:

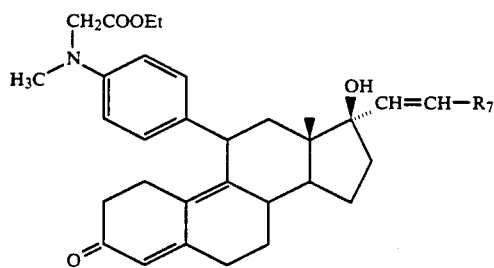

V''<sub>a</sub>

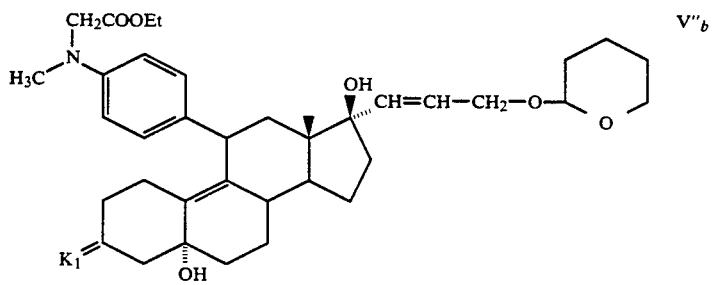

V''<sub>b</sub> or the products of formulae VI''<sub>a</sub> and VI''<sub>b</sub>

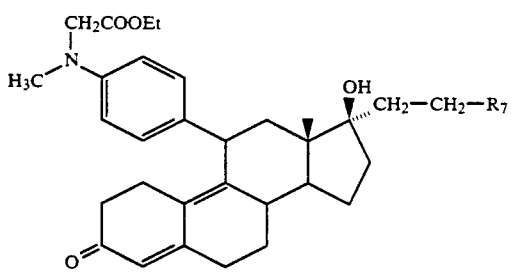

(VI''<sub>a</sub>)

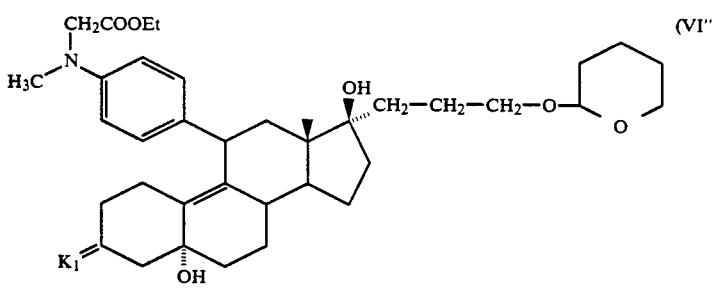

(VI''<sub>b</sub>)

which products of formulae V''<sub>b</sub> and VI''<sub>b</sub>, by an acid treatment, lead to the products of formulae V'''<sub>c</sub> and VI''<sub>c</sub>

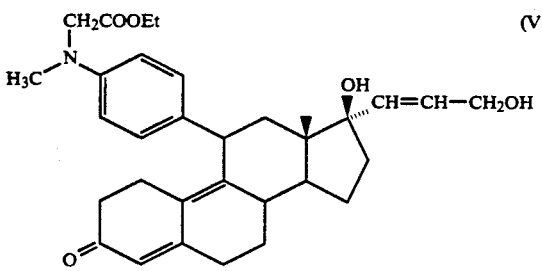

(V'''<sub>c</sub>)

-continued

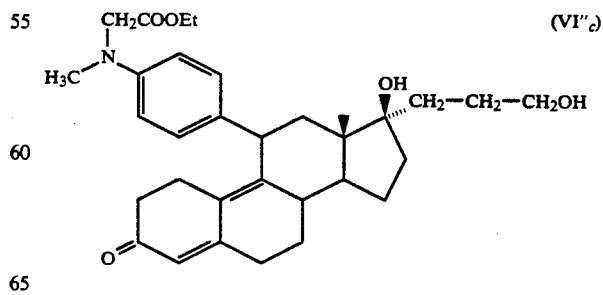

(VI''<sub>c</sub>)

while the products of formulae V'''<sub>c</sub> and VI''<sub>c</sub>, if desired, are reacted with tosyl chloride in pyridine to obtain the products of formulae V'''<sub>d</sub> and VI''<sub>d</sub> respectively:

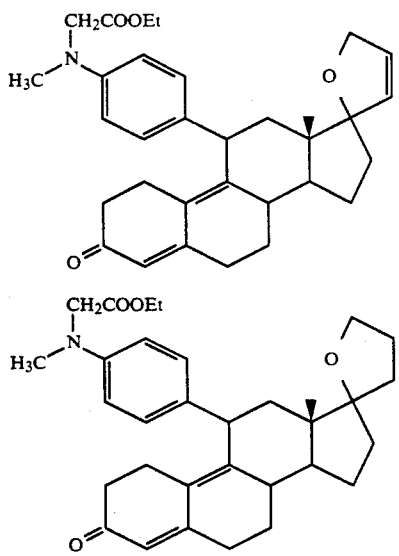

which products of formulae IV"$_a$, V"$_a$, V"$_c$, VI"$_a$, VI"$_c$, V"$_d$ and VI"$_d$ are treated with a hydro-alcohol solution of sodium hydroxide, then if desired, with hydrochloric acid, to obtain the products of formula I".

The nitrogenated base used with ethyl bromoacetate is preferably triethylamine. The hydrogenation of the triple bonds into double bonds takes place in the presence of a catalyst such as palladium hydroxide on barium sulfate and complete hydrogenation into a single bond takes place preferably in the presence of [chloro tris (triphenylphosphine) rhodium].

Some of the products of formula III used as starting materials are commercially-available products and the others can be prepared by methods known to a man skilled in the art, such as for example that described in MOUREU et al TAMPIER, Reports of the Academie des Sciences, Vol. 172, p. 1268 and Annales de Chimie 9, Vol. 15, p. 233. The products of formula II$_a$ and II$_b$ are generally known and their preparation is described in European Patent Nos. 0,262,188; 0,097,572 and 0,057,115 and in French Patent Nos. 2,566,779 and 2,620,707.

The products of formula (IV$_a$) and (IV$_b$) are new industrial products.

The novel anti-glucocorticoid compositions of the invention are comprised of an anti-glucocorticoidally effective amount of at least one compound of formula I and an inert pharmaceutical carrier. The compositions may be in the form of tablets, dragees, gelatin capsules, granules, suppositories, vaginal suppositories, ointments, creams and gels.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions are useful for combatting the side-effects of glucocorticoids; they also allow the combatting of disorders due to a hypersecretion of glucocorticoids and in particular the combatting of glaucoma, atherosclerosis, osteoporosis, diabetes, obesity, as well as the depression of immunity and insomnia.

The compositions also have progestomimetic or anti-progestomimetic, androgen or anti-androgen activities as well as anti-proliferative, anti-glucocorticoid, anti-estrogen and/or estrogen properties.

The products which possess anti-progestomimetic properties can be used to prepare original contraceptives or as agents for interrupting pregnancy. The products can also be used as period inducers for women and more generally for female warm-blooded animals.

These products are administered during periods when progesterone plays an essential physiological role, notably during the luteal phase of the cycle, at the moment of nidation (or implantation of the embryo) and during pregnancy. A method of contraception of the invention consists of administering to the woman at least one of the products of formula I for 1 to 5 days, preferably at the end of the cycle. This product is preferably administered orally or in vagino, but it can also be used parenterally. The compositions can also be used endonasally.

The compositions which possess anti-progestomimetic properties can also be used for hormonal disturbances and they can also be useful in the treatment of hormonal dependent tumors. Their actions on hypophysial secretions make the products usable in the menopause.

The products can also be used in the synchronization of estrus in farm animals, particularly bovines and ovines as well as to control the fertility of animals such as dogs and cats. The products can also show progestomimetic properties and can thus be used in the treatment of amenorrhea, dysmenorrhea and luteal insufficiencies.

The products which show anti-androgen properties can be used in the treatment of hypertrophies and cancer of the prostate, virilism, anaemia, hirsutism, and acne and for male contraceptives.

Finally, the products which show anti-proliferative, anti-estrogen and/or estrogen properties can be used in the treatment of hormonal-dependent carcinomas, such as for example mammary carcinomas and their metastases. These properties make the products usable also in the treatment of benign tumors of the breast. The estrogen properties make them usable also in the treatment of disorders linked to a hypofolliculinemia, for example amenorrhea, dysmenorrhea, repeated abortions, premenstrual disorders, as well as in the treatment of the menopause.

The novel method of the invention for inducing anti-glucocorticoid activity in warm-blooded animals, including humans, comprises administering to warm-blooded animals an anti-glucocorticoidally effective amount of at least one compound of formula I. The compounds may be administered orally, rectally, parenterally or topically and the usual daily dose is 0.1333 to 13.33 mg/kg depending on the condition treated, the specific compound and the method of administration.

In the following examples there are described several preferred embodiments to illustrate the invention. However, it should be understood that the invention is not intended to be limited to the specific embodiments.

EXAMPLE 1

Sodium salt of
[[4-[17α-(1-propynyl)-Δ$^{4,9}$-estradien-17β-ol-3-one-11β-yl]-phenyl]-methylamino]-acetic acid

STEP A: Ethyl [[4-[17α-(1-propynyl)-Δ$^{4,9}$-estradien-17β-ol-3-one 11β-yl]-phenyl]-methylamino]-acetate 1.66 g of 11-[4-(methylamino)-phenyl]-17α-(1-propynyl)- Δ$^{4,9}$-estradien-17β-ol-3 -one were dissolved in 3.2 ml of triethylamine in 60 ml of benzene and the solution was refluxed in a nitrogen atmosphere. 3.2 ml of ethyl bromoacetate were added and after cooling, the reaction medium was diluted with an aqueous solution of sodium bicarbonate. After decantation, the organic phase was washed with water, dried, then distilled to dryness. After chromatography of the residue on silica and elution with a cyclohexane-ethyl acetate (1-1) mixture, 2 g of the product were crystallized from a methylene chloride-isopropyl ether mixture to obtain 1.7 g of the sought product melting at approx. 110° C. and having a specific rotation of $[α]_D = +120°$ (c = 1% in $CHCl_3$) and a Rf = 0.36 [thin layer chromatography; support $SiO_2$; eluant: cyclohexaneethyl acetate (1-1) mixture].

STEP B: Sodium salt of [[4-[17α-(1-propynyl)-Δ$^{4,9}$-estradien-17β-ol-3-one-11β-yl]-phenyl]-methylamino] acetic acid 0.5 g of the ester of Step A was treated with 1 ml of N sodium hydroxide in 10 ml of absolute ethanol at ambient temperature and after 15 hours at this temperature, the solution was evaporated to dryness under reduced pressure. The residue was dissolved in a minimum of ethanol at 50% in water and chromatographed on Lichrosorb KC 18 ®, first eluting with methanol at 70% in water, then with methanol at 50% in water to obtain 0.35 g of the sought product with a specific rotation $[α]_D = +137°$ (c = 1% in EtOH) and a Rf0.6 [thin layer chromatography; support Silica KC 18 Whatman ®; eluant: aqueous solution of methanol at 70%).

EXAMPLE 2

Sodium salt of
[[4-[17α-(3-hydroxy-1-propynyl)-Δ$^{4,9}$-estradien-17β-ol-3-one-11 β--yl]-phenyl]-methylamino] acetic acid

STEP A: Ethyl [[4-[3,3-1,2-ethanediylbis-(oxy)-17α-[3-(( tetrahydro-2H-2-pyrranyloxy-1-propynyl)-Δ$^{4,9}$-estren-5α, 17β-diol-11β-yl]-phenyl ]-methylamino] acetate 7.1 g of (ethanediyl) acetal-cyclic of 11β-[4-(methylamino)-phenyl]-17α-[3-(tetrahydro-2 -pyrranyloxy)-1-propynyl]-Δ$^9$ -estren-5α,17α-[3-one were dissolved in 8 ml of triethylamine in 140 ml of tetrahydrofuran and a solution of 5 ml of ethyl bromoacetate in 25 ml of tetrahydrofuran were then added at reflux over 50 minutes. After 3 hours of stirring at reflux, 1 ml of trimethylamine and then 0.5 ml of ethyl bromoacetate were added. The reaction medium was left for one hour under reflux and after cooling, the reaction medium was poured into an aqueous solution of sodium bicarbonate and extracted with ethyl acetate. The organic phase was washed with water, dried and evaporated under reduced pressure. The residue was chromatographed on silica and eluted with a cyclohexane-ethyl acetate (1-1) mixture to obtain 5.6 g of the sought product with a Rf = 0.32 [thin layer chromatography; support Silica; eluant:cyclohexane-ethyl acetate (1-1) mixture].

STEP B: Ethyl [[4-17α-(3-hydroxy-1-propynyl)-Δ$^{4,9}$-estradien-17β-ol-3-one-11 β-yl]-phenyl]-methylamino] acetate 0.5 g of the product of Step A was dissolved in 5 ml of methanol with 5 ml of 2N hydrochloric acid and the solution was left for 2 hours at ambient temperature, then neutralized with an aqueous solution of sodium bicarbonate and extracted with methylene chloride. The organic phase was washed with water, dried and evaporated to dryness to obtain a crude product which was crystallized from ether to obtain 0.32 g of the sought product melting at 140° C. (approx.) and having a specific rotation of $[α]_D = +109°$ (c = 1% in $CHCl_3$) and a Rf = 0.53 [thin layer chromatography; support: silica; eluant: ethyl acetate].

STEP C: Sodium salt of [[4-17 α-(3-hydroxy-1-propynyl)-Δ$^{4,9}$-estradien-17β-ol-3-one -11β-yl]-phenyl]-methylamino] acetic acid 0.32 g of the product of Step B were dissolved in 1.5 ml of methanol and 0.55 ml of N sodium hydroxide at 60° C. under nitrogen. After 80 minutes at this temperature, the mixture was cooled down and chromatographed on Bondapack C 18 ® eluting with a methanol-water (25-75) mixture, then a (30-70) mixture to obtain 280 mg of the sought product with a specific rotation of $[α]_D = +133°$ (c = 1% in EtOH).

EXAMPLE 3

Sodium salt of
(Z)-[[4-[17α-(3-hydroxy-1-propenyl)-Δ$^{4,9}$-estradien-17β-ol-3-one -11β-yl]-phenyl]-methylamino] acetic acid

STEP A: Ethyl (Z)-[[4-[3,3-[1,2-ethanediylbis-(oxy)-17α-(3-tetrahydro-2H-2-pyrranyloxy -1-propenyl]-Δ$^9$estren-5α17β-diol-11β-yl]-phenyl]-methylamino]-acetate and its (E) isomer 0.8 g of the product of Step A of Example 2 were dissolved in 16 ml of ethyl acetate with 0.3 ml of pyridine and 12 ml of palladium hydroxide on barium sulfate at 10% were added to the solution. The mixture was hydrogenated for 40 minutes (absorption of 27.1 ml of hydrogen). After purging with nitrogen, the catalyst was separated and the filtrate was evaporated to dryness to obtain 0.8 g of a mixture of isomers (E) and (Z) which were separated by chromatography on silica and elution with a cyclohexane-ethyl acetate (1-1) mixture to obtain 0.655 g of isomer (Z) and 0.065 g of isomer (E) of the desired product.

STEP B: Ethyl (Z) [[4-[17α-(3-hydroxy-1-propenyl)-Δ$^{4,9}$-estradien-17β-ol-3-one -11β-yl]-phenyl]-methylamino] acetate 6.3 g of the product (isomer (Z)) of Step A were dissolved in 60 ml of methanol and 60 ml of 2N hydrochloric acid were added. The solution stood for 5 hours at ambient temperature and then was carefully poured into an aqueous solution of sodium bicarbonate and extracted with methylene chloride. The organic phase was washed with water, dried, then evaporated to dryness under reduced pressure to obtain 5.27 g of a mixture which was chromatographed on silica and eluted with a cyclohexane-ethyl acetate (2-8) mixture to obtain 3.76 g of the sought product. 500 mg of the product were purified by crystallization from an ether-isopropyl ether mixture to obtain 0.486 g of purified product melting at 163° C. and having a specific rotation of $[\alpha]_D = +20°$ (c=1% in chloroform) and a Rf=0.29 [thin layer chromatography; support: silica; eluant: cyclohexane-ethyl acetate (2-8) mixture].

STEP C: Sodium salt of (Z) [[4-[17α-(3-hydroxy-1-propenyl)-Δ$^{4,9}$-estradien-17β-ol-3 one-11β-yl]-phenyl]-methylamino] acetic acid 0.78 g of the product of Step B were dissolved in 3.5 ml of methanol and 1.5 ml of N sodium hydroxide at 60° C. under inert atmosphere and heating was maintained for 1 hour. The solution was cooled and chromatographed on Bondapack ® KC 18 eluting with a methanol-water (4-6) mixture and the eluants were lyophilized to obtain 0.712 g of the desired product with a specific rotation of $[\alpha]_D = +202°$ (c=1% in EtOH) and a Rf=0.60 [thin layer chromatography: support: silica KC 18 Whatman ®; eluant: methanol-aqueous solution of 0.05M ammonium acetate (65-35)].

EXAMPLE 4

( Sodium salt of [[4-[17α-(3-hydroxy-propyl)-Δ$^{4,9}$-estradien-17β-ol-3-one-11 β-yl]-phenyl]-methylamino] acetic acid STEP A: Ethyl [[4-[3,3-[ethanediylbis-(oxy)17α-[3-(tetrahydro-2H-2-pyrranyloxy)-propyl)-Δ$^{4,9}$-estren-17β-ol-3-one-11β-yl]-phenyl]-methylamino] acetate 5.6 g of the product of Step A of Example 2 were dissolved in 70 ml of toluene and 1.38 g of Wilkinson reagent [chlorotris(triphenyl phosphine) rhodium] were added. Hydrogenation took place until saturation was reached and after evaporation under vacuum, 7.2 g of a red resin were obtained which, after chromatography on silica eluting with a cyclohexane-ethyl acetate (1-1) mixture yielded 5.6 g of the sought product.

STEP B: Ethyl [[4-[17α-(3-hydroxy-propyl)-Δ$^{4,9}$-estradien-17β-ol-3-one-11 β-yl]-phenyl]-methylamino] acetate 5.6 g of the product of Step B were dissolved in 50 ml of methanol with 50 ml of 2N hydrochloric acid and after standing for 2 hours at ambient temperature, the mixture was poured into an aqueous solution of sodium bicarbonate and extracted with methylene chloride. The organic phase was washed with water, dried and evaporated to dryness. The residue was chromatographed on silica and eluted with cyclohexane-ethyl acetate (2-8) mixture to obtain after crystallization from ether, 2.286 g of the desired product melting at 100° C. and having a specific rotation of $[\alpha]_D = +175°$ (c=1% in CHCl₃) and a Rf=0.30 [thin layer chromatography; support: silica; eluant: ethyl acetate].

STEP C: Sodium salt of [[4-[17α-(3-hydroxy-propyl)-Δ$^{4,9}$-estradien-17 β-ol-3-one-11β-yl]-phenyl]-methylamino] acetic acid A solution of 1.5 ml of N sodium hydroxide in 4 ml of methanol was degassed with nitrogen bubbled through and 0.8 g of the product of Step B were introduced into it. After heating at 80° C. for 1 hour, the solution was cooled and chromatographed on a Bondapack column eluting with a methanol-water (3-7) mixture. The eluants were lyophilized to obtain 0.637 g of the desired product with a specific rotation of $[\alpha]_D = +179°$ (c=0.95% in EtOH).

EXAMPLE 5

Sodium salt of [[4-[3-oxo-spiro-[Δ$^{4,9}$-estradien-17β,2'(5H)-furan]-11β-yl ]-phenyl]-methylamino] acetic acid STEP A: Ethyl [[4-3-oxo-spiro-[Δ$^{4,9}$-estradien-17β,2-(5H)-furan]-11β-yl]-phenyl ]-methylamino] acetate 2.08 g of the product of Step B of Example 3 were dissolved in 40 ml of pyridine and the solution was cooled to 0° C. 4 g of tosyl chloride were added with stirring and the temperature was taken to ambient temperature. The solution was allowed to react for 4 hours and after dilution with water whilst cooling, extraction with methylene chloride was effected. Then, the organic phase was washed with water, dried and evaporated under reduced pressure. The crude product was chromatographed on silica eluting with a cyclohexane-ethyl acetate (1-1) mixture to obtain 1 74 g of the desired product with a specific rotation of $[\alpha]_D = 229°$ (c=1% in CHCl₃) and a Rf=0.38 [thin layer chromatography; support: silica; eluant: cyclohexane-ethyl acetate (6-4) mixture].

STEP B: Sodium salt of [[4-[3-oxo-spiro-[Δ$^{4,9}$-estradien-17β,2'(5H)-furan]-11β-yl-phenyl-methylamino]-acetic acid 1.01 g of the product of Step A were dissolved in 30 ml of methanol and 2 ml of N sodium hydroxide and the solution was stirred under nitrogen for 15 and a half hours, then evaporated under reduced pressure without heating. The residue was chromatographed on Bondapack KC 18 ® eluting with a methanol-water (45-55 mixture and the eluant was lyophilized to obtain 0.655 g of the desired salt with a specific rotation of $[\alpha]_D = +253°$ (c=1% in ETOH).

EXAMPLE 6

Sodium salt of [[4-[4',5'dihydro-3-oxo-spiro-[Δ$^{4,9}$-estradien-17β,2'(3'H)-furan]-11β-yl]-phenyl]-methylamino acetate STEP A: Ethyl [[4-[4',5'-dihydro-3-oxo-spiro-[Δ$^{4,9}$-estradien-17β,2'(3'H)-furan]-11β-yl-phenyl-methylamino] acetate 1.71 g of the product of Step B of Example 4 were dissolved in 34 ml of pyridine and after cooling the solution to 0° C., 1.7 g of tosyl chloride were added with stirring. The reaction medium was taken to ambient temperature and stood for 3 hours. A few pieces of ice, then water were added and the mixture was extracted with ethyl acetate. The organic phase was washed with water, dried and evaporated to dryness and the residue was chromatographed on silica eluant: cyclohexane-ethyl acetate (7-3) to obtain 1.375 g of sought product with a specific rotation of $[\alpha]_D = +174°$ (c=1% in CHCl₃) and a Rf=0.33 [thin layer chromatography; support: silica; eluant: cyclohexane-ethyl acetate (7-3) mixture].

STEP B: Sodium salt of
[[4-4',5'-dihydro-3-oxo-spiro-$\Delta^{4,9}$-estradien-17$\beta$,2'(3'H)-furan]-11$\beta$-yl]-phenyl]-methylamino] acetic acid 0.92 g of the product of Step A were dissolved in 9 ml of methanol and 1.8 ml of N sodium hydroxide and after 1 hour of heating in an oil bath at 70° C. under inert atmosphere, the solution was concentrated to dryness. The residue was chromatographed on Bondapack® (10 microns) eluting with a methanol-water (30-70) mixture, then a (50-50) mixture and the eluant was lyophilized to obtain 0.65 g of the desired salt with a specific rotation of $[\alpha]_D = +187°$ (c=1% in ethanol).

EXAMPLE 7

Sodium salt of
[[4-17$\alpha$-(2-propynyl)-$\Delta^{4,9}$-estradien-17$\beta$-ol-3-one-11$\beta$-yl]-phenyl]-methylamino] acetic acid STEP A: Ethyl
[[4-[17$\alpha$-(2-propynyl)-$\Delta^{4,9}$-estradien-17$\beta$-ol-3-one-11$\beta$-yl]-phenyl]-methylamino] acetate 1 178 g of 11$\beta$-[4-(methylamino)-phenyl]-17$\beta$-(2-propynyl) $\Delta^{4,9}$-estradien-17$\beta$-ol-3-one were dissolved in 41 ml of toluene with 2.3 ml of triethylamine and 2.3 ml of ethyl bromoacetate were added. The solution was stirred for 1 and a half hours at 80° C., cooled and then diluted with a saturated aqueous solution of sodium bicarbonate. The aqueous phase was decanted and re-extracted with ethyl acetate. The organic phase was washed with water, dried on sodium sulfate and evaporated to dryness under reduced pressure. The residue was chromatographed on silica eluting with an ethyl acetate-essence G (50-50) mixture to obtain 1.038 g of product which was crystallized from a methylene chloride-isopropyl ether mixture to obtain 0.968 g of the d<sired product melting at 195° C. and having a Rf0.25 [thin layer chromatography; support: silica F$_{254}$ Merck 60$^R$; eluant: cyclohexane-ethyl acetate (7-3) mixture].

STEP B: Sodium salt of
[[4-[17$\alpha$-(2-propynyl)-$\Delta^{4,9}$-estradien-17$\beta$-ol-3-one-11$\beta$-yl]-phenyl]-methylamino] acetic acid 0.894 g of the product of Step A were dissolved in 18 ml of absolute ethanol with 1.8 ml of N sodium hydroxide and after 9 hours of stirring at ambient temperature, 13 ml of absolute ethanol were added and stirring was continued for 25 hours. The solution was filtered and the filtrate was evaporated to dryness under reduced pressure. The residue was chromatographed on Bondapack KC 18 ® eluting with a methanol-water mixture at (30-70), then with (50-50). The eluant was concentrated under reduced pressure to eliminate the methanol, filtered on a 45 μ millipore membrane and lyophilized to obtain 0.704 g of the desired product with a specific rotation of $[\alpha]_D = +92° +3°$ (c=1% in EtOH) and a Rf =0.73 ({thin layer chromatography; support: KC 18 Whatman®; eluant: methanol-water mixture (70-30)}.

EXAMPLE 8

Sodium salt of
[[4-17$\alpha$-(2-propenyl)-$\Delta^{4,9}$-estradien-17$\beta$-ol-3-one 11$\beta$-yl]-phenyl]-methylamino] acetic acid STEP A: Ethyl
[[4-[17$\alpha$-(2-propenyl)-$\Delta^{4,9}$-estradien-17$\beta$-ol-3-one 11$\beta$-yl]-phenyl]-methylamino] acetate Using the procedure of Step A of Example 7, 1.068 g of 11$\beta$-[4-(methylamino)-phenyl]-17$\alpha$-(2-propenyl) -$\Delta^{4,9}$-estradien-17$\beta$-ol-3-one in 37 ml of toluene were reacted with 2.1 ml of triethylamine and 2.1 ml of ethyl bromoacetate to obtain after crystallization from a methylene chloride-isopropyl ether mixture, 1.151 g of the desired product in the form of white crystals melting at 191° C. and having a Rf=0.27 [thin layer chromatography; support: silica F$_{254}$ Merck 60$^R$; eluant: ethyl acetate-essence G (50-50) mixture].

STEP B: Sodium salt of
[[4-17$\alpha$-(2-propenyl)-$\Delta^{4,9}$-estradien-17$\beta$-ol-3-one -11$\beta$-yl]-phenyl]-methylamino] acetic acid 1.079 g of the product of Step A were dissolved in 22 ml of ethanol and 2.17 ml of N sodium hydroxide and after 3 hours of stirring at ambient temperature, 3 ml of ethanol were added and stirring was continued for 23 hours. The solution was filtered and the filtrate was evaporated under reduced pressure. The residue was chromatographed on KC 18 Bondapack ® eluting with a methanol-water mixture at (30-70), then with a (50-50) mixture and the eluant was concentrated to eliminate the methanol, filtered and lyophilized to obtain 0.878 g of the desired salt with a specific rotation of $[\alpha]_D = +203° +3°$ (c=1% in ETOH) and a Rf=0.63 [thin layer chromatography; support KC ® Whatman®; eluant: methanol-water (7-3) mixture].

EXAMPLE 9

Sodium salt of
[[4-[21-chloro-19-nor-17$\alpha$-$\Delta^{4,9}$-pregnadien-17$\beta$-ol-3-one-20 -yn-11$\beta$-yl]-phenyl]-methylaminoacetic acid STEP A:
[[4[21-chloro-19nor-17$\alpha$-$\Delta^{4,9}$-pregnadien-17$\beta$-ol-3-one-20-yn-11 $\beta$-yl]-phenyl]-methylamino] acetic acid 1.38 g of 21-chloro-11$\beta$-[4-(methylamino)-phenyl]-19-nor-17$\alpha$-$\Delta^{4,9}$-pregnadien-17 $\beta$-ol-3-one-20-yn were dissolved in 47 ml of toluene with 2.5 ml of triethylamine and after adding 2.5 ml of ethyl bromoacetate, the solution was stirred for 2 hours at 80° C., then cooled. A saturated aqueous solution of sodium bicarbonate was added and the aqueous phase was decanted. The organic phase was washed with water, dried on sodium sulfate and evaporated to dryness under reduced pressure. The crude product was chromatographed on silica eluting with a ethyl acetate-essence G (40-60) mixture and after crystallization from a methylene chlorideisopropyl ether mixture, 1.555 g of the desired ester melting at 105° C. and having a Rf=0.27 [thin layer chromatography; support: silica; eluant: ethyl acetate-essence G (1-1) mixture] were obtained.

STEP B: Sodium salt of
[[4-[21-chloro-19-nor-17$\alpha$-$\Delta^{4,9}$-pregnadien-17$\beta$-ol-3-one-20-yn-11$\beta$-yl]-phenyl]-methylamino] acetic acid 1.494 g of the product of Step A were dissolved in 29 ml of absolute ethanol and 2.9 ml of N sodium hydroxide and the solution was stirred for 22 hours and 30 minutes at ambient temperature, filtered and the filtrate was evaporated to dryness. The residue was chromatographed on Bonapack KC 18, eluting with a methanol-water mixture at (30-70), then with a mixture at (50-50). The eluant was concentrated to eliminate the methanol, filtered and lyophilized to obtain 1.23 g of the desired salt with a specific rotation of $[\alpha]_D = 124° + 2.5°$ (c=1% in EtOH) and a Rf=0.67 [thin layer chromatography; support: KC 18 Whatman ®; eluant: methanol-water (70-30) mixture].

EXAMPLE 10

A collyrium was prepared containing 2 g of the product of Example 1 and sufficient excipient of distilled water, sodium chloride, methylcellulose and sodium borate to obtain 100 ml.

PHARMACOLOGICAL STUDY

1) Measurement of the relative bond affinity for the receptors of steroid hormones:

Glucocorticoid receptor of rat's thymus

Male rats weighing 160 to 200 g were suprarenalectomized and 4 to 8 days after this removal, the animals were killed. The thymuses were removed and homogenized at 0° C. using a Potter teflon-flask in a (TSD) 10 mM Tris, 0.25M saccharose, 2mM dithiothreitol, HCl, pH 7.4 buffer (1 g of tissue per 10 ml of TSD). The homogenate was ultracentrifuged at 105,000 g×90 mn at 0° C. and aliquots of the supernatant or "cystosol" were incubated at 0° C. for 4 hours and 24 hours with constant concentration (T=2.5 nM) of tritiated dexamethasone in the presence of increasing concentrations (0–2,500 nM) of cold dexamethasone or of the cold product under test. The concentration of the bonded tritiated dexamethasone (B) was then measured in each incubate by the technique of adsorption with carbon-dextran.

Progesterone receptor of rabbit's uterus

Impuberal female rabbits weighing about 1 kg received a cutaneous application of 25 μg of estradiol and five days after this treatment, the animals were killed. The uteruses were removed, weighed and homogenised at 0° C. using a Potter teflon-flask ina (TS) 10 mM Tris, 0.25M saccharose, HCl pH 7.4 buffer (1 g of tissue per 50 ml of TS). The homogenate was ultra-centrifuged at 105,000 g×90 mn at 0° C. and aliquots of the supernatant or "cytosol", were incubated at 0° C. for 2 hours and 24 hours with a constant concentration (T=5 nm) of tritiated R 5020 (17,21-dimethyl-19-nor-$\Delta^{4,9}$-pregnadien-3, 20-dione, strongly progestomimetic mimetic having a great affinity for the progesterone receptor), in the presence of increasing concentrations (0–2500 nM) of cold progesterone, or of the product under test. The concentration of bonded tritiated R 5020 (B) was measured in each incubate by the technique of adsorption with carbon-dextran.

Androgen receptor of rat's prostate

Male rats weighing of 160 to 200 g were castrated and 24 hours after the castration, the animals were killed. The prostates were removed, weighed and homogenized at 0° C. using a Potter Teflon-flask in a (TSDPM) 10 mM Tris, 0.25 M saccharose, 0.1 mM phenyl methane sulfonyl fluoride, 20 mM molybdate, 2mM dithiothreitol, HCl pH 7.4 buffer (1 g of tissue per 5 ml of TSDPM). The homogenate was ultracentrifuged at 105,000 g×60 mn at 0° C. and aliquots of the supernatant or "cytosol" were incubated at 0° C. with a constant concentration of tritiated testosterone in the presence of increasing concentrations (0–1000 nM) of cold testosterone or of the product under test. After half an hour and 24 hours of incubation, the concentration of bonded tritiated testosterone (B) was measured in each incubate by the technique of adsorption with carbon-dextran.

Calculation of the relative bond affinity

The calculation of the relative bond affinity (RBA) was identical for all receptors. The following two curves were drawn: the percentage of bonded tritiated hormone B/T as a function of the logarithm of the concentration of the cold reference hormone and B/T as a function of the logarithm of the concentration of the cold product under test.

The straight line of the equation:

$$I_{50} = \left( \frac{B}{T} \max + \frac{B}{T} \min \right)/2$$

was determined.

B/T max = Percentage of bonded tritiated hormone for an incubation of this tritiated hormone at the concentration (T).

B min = Percentage of bonded tritiated hormone for an incubation of this tritiated hormone at this concentration (T) in the presence of a great excess of cold hormone ($2500 \times 10^{-9}$).

The intersections of the straight line $I_{50}$ and the curves allow the evaluation of the concentrations of the cold reference hormone (CH) and of the cold product under test (CX) which inhibit by 50% the bonding of the tritiated hormone on the receptor. The relative bond affinity (RBA) of the product under test was determined by the equation RBA=100 (CH)/(CX)

The results obtained are the following:

| Examples | Progesterone 2H | 24H | Glucocorticoid 4H | 24H | Androgen 0,5H | 5H |
|---|---|---|---|---|---|---|
| 1 | 22 | 107 | 101 | 129 | 2,1 | 10,1 |

2) Anti-glucocorticoid activity vis-a-vis dexamethasone

Study in vitro Incorporation of uridine in rat thymocytes

Glucocorticoids cause an inhibition of the incorporation of nucleosides in lymphoid tissue and the measurement of the incorporation of radio-active uridine in the thymocytes in the presence of a product under test allows its glucocorticoid activity to be evaluated.

In accordance with the technique described by Dausse et al (3), the thymus of a suprarenalectomized rat weighing 160 to 180 g was removed, shredded and homogenized slowly using a teflon-flask homogenizer in Hanks solution. The cellular suspension was filtered on gauze, then centrifuged at 800 g×10 mn. A new centrifugation was carried out at 800 g×10 mm and the deposit was suspended in a nutritive medium (M.E.M. Gibco). The cellular concentration was adjusted to approximately $20 \times 10^6$ cells per ml and aliquots of 250

μl were incubated under carbogen for 3 hours at 37° C. with 5×10⁻⁸M of dexamethasone in the presence or not of increasing concentrations of product (10⁻⁸ to 10⁻⁶M). 0.1 uCi of tritiated uridine was added to each incubate and the incubation was continued for one hour. The incubates were cooled and 1 ml of a cold solution of trichloroacetic acid (TCA) at 5% weight/volume was added. The precipitates were collected on Whatman GF/C filters and were washed with 4×2 ml of 5% iced TCA. The radioactivity retained on the filters (representing the tritiated uridine incorporated in the thymocytes) was measured using a liquid scintillation spectrometer.

| Product of Example | $10^{-6}$M | $10^{-7}$M | $10^{-8}$M |
|---|---|---|---|
| 1 | 82 | 42 | 3 |
| 2 | 37 | 0 | 0 |

The preceding measurements show that the product of Example 1 shows a good anti-glucocorticoid activity.

Various modifications of the products and processes of the invention may be made without departing from the spirit or scope thereof and it is to be understood that the invention is intended to be limited only as defined in the appended claims.

What we claim is:

1. A compound of the formula

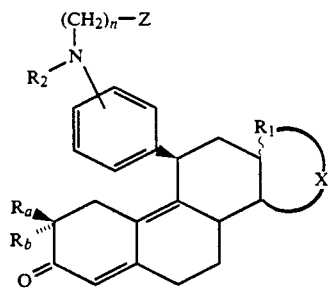

(I)

wherein $R_1$ is an aliphatic hydrocarbon of 1 to 8 carbon atoms, $R_a$ and $R_b$ are individually hydrogen or alkyl of 1 to 4 carbon atoms, $R_2$ is hydrogen or optionally substituted alkyl of 1 to 12 carbon atoms, n is an integer from 1 to 6, Z is free carboxy or salified with an alkali metal, alkaline earth metal or $NH_4$ and X is the remainder of an optionally unsaturated 5 member ring optionally substituted with a member selected from the group consisting of

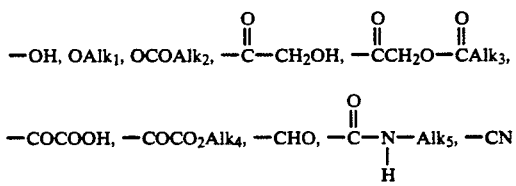

optionally substituted alkyl, alkenyl and alkynyl of 2 to 8 carbon atoms, $Alk_1$, $Alk_2$ and $Alk_5$ are individually alkyl of 1 to 8 carbon atoms or aralkyl of 7 to 15 carbon atoms, $Alk_3$ is optionally substituted alkyl of 1 to 8 carbon atoms or aralkyl of 7 to 15 $Alk_4$ is alkyl of 1 to 8 carbon atoms and the wavy line indicates the α- or β-position for $R_1$.

2. A compound of claim 1 having the formula

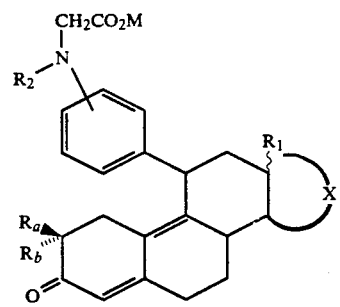

(I')

wherein M is hydrogen or sodium and $R_1$, $R_2$, $R_a$, $R_b$ and X have the definition of claim 1.

3. A compound of claim 1 wherein X is the remainder of the ring

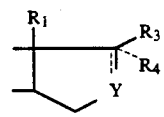

wherein $R_1$ has the definition of claim 1 and the dotted line indicates the optional presence of a double bond, Y is

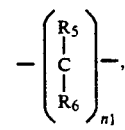

$n_1$, is 1 or 2, $R_5$ is selected from the group consisting of hydrogen, alkyl of 1 to 8 carbon atoms, alkenyl and alkynyl of 2 to 8 carbon atoms, aryl of 6 to 14 carbon atoms and aralkyl of 7 to 15 carbon atoms, $R_6$ is selected from the group consisting of hydrogen, —OH, alkyl of 1 to 8 carbon atoms, alkenyl and alkynyl of 2 to 8 carbon atoms, aryl of 6 to 14 carbon atoms and aralkyl of 7 to 15 carbon atoms, $R_3$ and $R_4$ are individually selected from the group consisting of hydrogen,

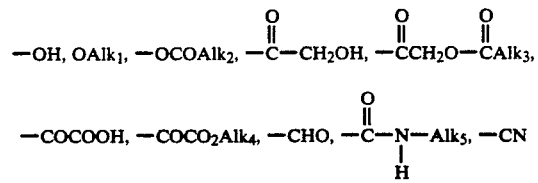

and optionally substituted alkyl, alkenyl and alkynyl of 2 to 8 carbon atoms, $Alk_1$, $Alk_2$, and $Alk_5$ are individually alkyl of 1 to 8 carbon atoms or aralkyl of 7 to 15 carbon atoms, $Alk_3$ is optionally substituted alkyl of 1 to 8 carbon atoms or aralkyl of 7 to 15 carbon atoms, $Alk_4$ is alkyl of 1 to 8 carbon atoms.

4. A compound of claim 1 wherein X is the remainder of the ring

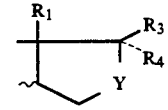

wherein R₁, R₃ and R₄ have the definitions of claim 3.

5. A compound of claim 1 of the formula

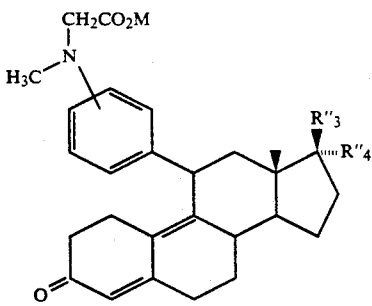 (I'')

wherein M is hydrogen or sodium, R''₃ is —OH and R''₄ is —C≡CR₇ or 2-propynyl or 2-propenyl, the dotted line indicates a possible second or third bond, R₇ is selected from the group consisting of hydrogen, halogen, trimethylsilyl and methyl optionally substituted with at least one member of the group consisting of halogen, —OH, alkoxy, alkylthio or alkylamino of 1 to 4 carbon atoms, dialkylamino of 2 to 8 carbon atoms and trialkylsilyl of 3 to 12 carbon atoms.

6. A compound of claim 1 which is the sodium salt of [[4-[17α-(1-propynyl)-Δ⁴,⁹-estradien-17 β-ol-3-one-11β-yl]-phenyl]-methylamino] acetic acid.

7. A compound having a formula selected from the group consisting of

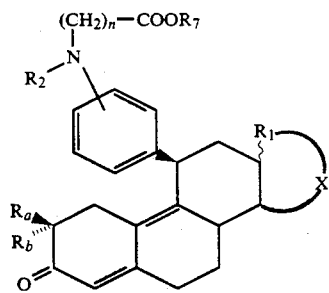 (IVₐ)

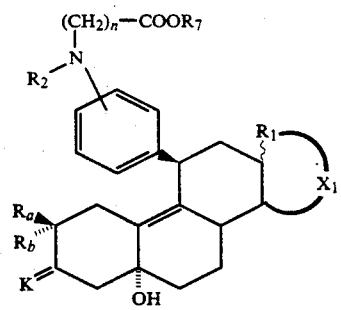 (IV_b)

wherein Rₐ, R_b, R₁, R₂ and X are as defined in claim 1, R₇ is alkyl of 1 to 4 carbon atoms optionally substituted with at least one phenyl and X is an oxo protective group.

8. An anti-glucocorticoid composition comprising an anti-glucocorticoidally effective amount of at least one compound of claim 1 and an inert carrier.

9. A composition of claim 8 wherein the active compound has the formula

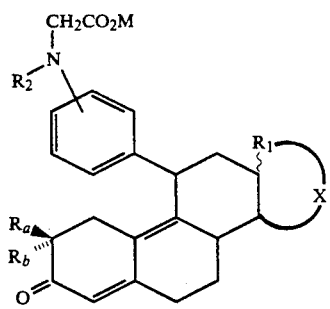 (I')

wherein M is hydrogen or sodium R₁, R₂, Rₐ, R_b and X have the definition of claim 1.

10. A composition of claim 8 wherein X is the remainder of the ring

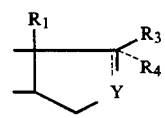

wherein R₁ has the definition of claim 1 and the dotted line indicates the optional presence of a double bond, Y is

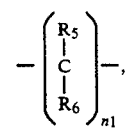

n₁ is 1 or 2, R₅ is selected from the group consisting of hydrogen, alkyl of 1 to 8 carbon atoms, alkenyl and alkynyl of 2 to 8 carbon atoms, aryl of 6 to 14 carbon atoms and aralkyl of 7 to 15 carbon atoms, R₆ is selected from the group consisting of hydrogen, —OH, alkyl of 1 to 8 carbon atoms, alkenyl and alkynyl of 2 to 8 carbon atoms, aryl of 6 to 14 carbon atoms and aralkyl of 7 to 15 carbon atoms, R₃ and R₄ are individually selected from the group consisting of hydrogen,

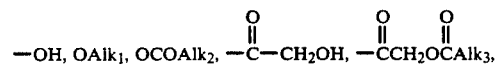

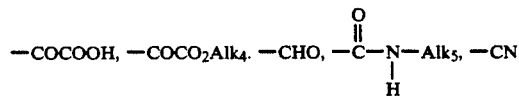

and optionally substituted alkyl, alkenyl and alkynyl of 2 to 8 carbon atoms, Alk₁, Alk₂ and Alk₅ are individually alkyl of 1 to 8 carbon atoms or aralkyl of 7 to 15 carbon atoms, Alk₃ is optionally substituted alkyl of 1 to 8 carbon atoms or aralkyl of 7 to 15 carbon atoms, Alk₄ is alkyl of 1 to 8 carbon atoms.

11. A composition of claim 8 wherein X is the remainder of the ring

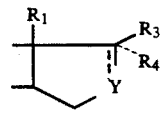

wherein R₁, R₃ and R₄ have the definitions of claim 10.

12. A composition of claim 8 wherein the active compound has the formula

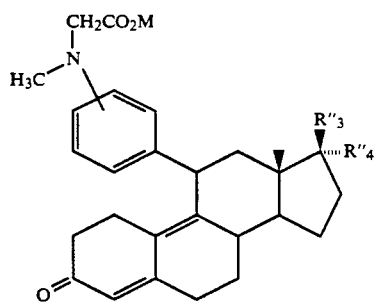
(I″)

wherein M is hydrogen or sodium, R″₃ is —OH and R″₄ is —C≡CR₇ or 2-propynyl of 2-propenyl, the dotted line indicates a possible third bond, R₇ is selected from the group consisting of hydrogen, halogen, trimethylsilyl and methyl optionally substituted with at least one member of the group consisting of halogen, —OH, alkoxy, alkylthio or alkylamino of 1 to 4 carbon atoms, dialkylamino of 2 to 8 carbon atoms and trialkylsilyl of 3 to 12 carbon atoms.

13. A composition of claim 8 wherein the active compound is the sodium salt of [[4-[17α-(1-propynyl)-Δ⁴,⁹-estradien-17β-ol-3-one-11β-yl ]-phenyl]-methylamino] acetic acid.

14. A method of inducing anti-glucocorticoid activity in warm-blooded animals comprising administering to warm-blooded animals an anti-glucocorticoidally effective amount of at least one compound of claim 1.

15. A method of claim 14 wherein the active compound has the formula

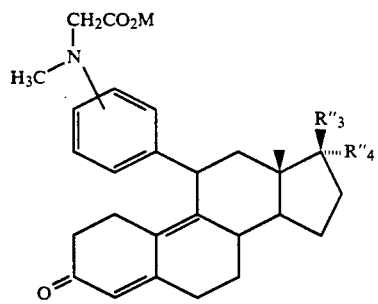
(I″)

wherein M is hydrogen or sodium and R₁, R₂, R_a, R_b and X have the definitions of claim 1.

16. A method of claim 14 wherein X is the remainder of the ring

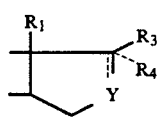

wherein R₁ has the definition of claim 1 and the dotted line indicates the optional presence of a double bond, Y is

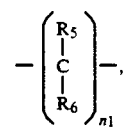

n₁ is 1 or 2, R₅ is selected from the group consisting of hydrogen, alkyl of 1 to 8 carbon atoms, alkenyl and alkynyl of 2 to 8 carbon atoms, aryl of 6 to 14 carbon atoms and aralkyl of 7 to 15 carbon atoms, R₆ is selected from the group consisting of hydrogen, —OH, alkyl of 1 to 8 carbon atoms, alkenyl and alkynyl of 2 to 8 carbon atoms, aryl of 6 to 14 carbon atoms and aralkyl of 7 to 15 carbon atoms, R₃ and R₄ are individually selected from the group consisting of hydrogen,

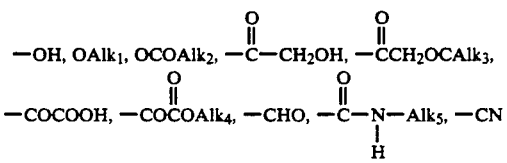

and optionally substituted alkyl, alkenyl and alkynyl of 2 to 8 carbon atoms, Alk₁, Alk₂ and Alk₅ are individually alkyl of 1 to 8 carbon atoms or aralkyl of 7 to 15 carbon atoms, Alk₃ is optionally substituted alkyl of 1 to 8 carbon atoms or aralkyl of 7 to 15 carbon atoms, Alk₄ is alkyl of 1 to 8 carbon atoms.

17. A method of claim 14 wherein X is the remainder of the ring

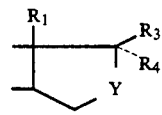

wherein R₁, R₃ and R₄ have the definition of claim 16.

18. A method of claim 14 wherein the active compound has the formula

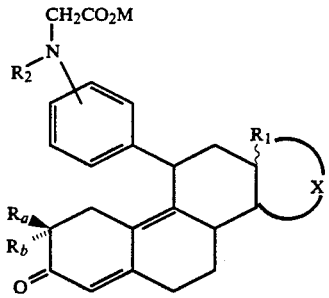
(I′)

wherein M is hydrogen or sodium, R″₃ is —OH and R″₄ is —C≡CR₇ or 2-propynyl or 2-propenyl, the dotted line indicates a possible third bond, R₇ is selected from the group consisting of hydrogen, halogen, trimethylsilyl and methyl optionally substituted with at least one member of the group consisting of halogen, —OH, alkoxy, alkylthio or alkylamino of 1 to 4 carbon atoms, dialkylamino of 2 to 8 carbon atoms and trialkylsilyl of 3 to 12 carbon atoms.

19. A method of claim 14 the sodium salt of [[4-[17α-(1-propynyl)-Δ⁴,⁹-estradien-17β-ol-3-one-11β-yl]-phenyl]-methylamino acetic acid.

* * * * *